(12) United States Patent
Radhakrishnan et al.

(10) Patent No.: US 10,869,647 B2
(45) Date of Patent: Dec. 22, 2020

(54) METHODS, SYSTEMS, AND DEVICES FOR ANALYZING LUNG IMAGING DATA

(71) Applicant: PulmonX Corporation, Redwood City, CA (US)

(72) Inventors: Sri Radhakrishnan, Cupertino, CA (US); Ryan Olivera, Granite Bay, CA (US)

(73) Assignee: Pulmonx Corporation, Redwood City, CA (US)

( * ) Notice: Subject to any disclaimer, the term of this patent is extended or adjusted under 35 U.S.C. 154(b) by 665 days.

(21) Appl. No.: 15/424,458

(22) Filed: Feb. 3, 2017

(65) Prior Publication Data
US 2017/0224301 A1 Aug. 10, 2017

Related U.S. Application Data

(60) Provisional application No. 62/291,889, filed on Feb. 5, 2016.

(51) Int. Cl.
| A61B 6/00 | (2006.01) |
| A61B 6/03 | (2006.01) |
| G06T 7/00 | (2017.01) |

(52) U.S. Cl.
CPC .......... *A61B 6/5217* (2013.01); *A61B 6/032* (2013.01); *A61B 6/50* (2013.01); *A61B 6/563* (2013.01); *G06T 7/0012* (2013.01); *A61B 6/5205* (2013.01); *G06T 2207/10081* (2013.01); *G06T 2207/30061* (2013.01)

(58) Field of Classification Search
CPC ......... A61B 6/5217; A61B 6/032; A61B 6/50; A61B 6/563; A61B 6/5205; G06T 7/0012; G06T 2207/10081; G06T 2207/30061

USPC .......................................................... 600/425
See application file for complete search history.

(56) References Cited

U.S. PATENT DOCUMENTS

2003/0055331 A1 3/2003 Kotmel et al.
2004/0010209 A1* 1/2004 Sirokman ............ A61B 5/1076
600/587

(Continued)

FOREIGN PATENT DOCUMENTS

WO WO-2017136781 A1 8/2017

OTHER PUBLICATIONS

Archer, DC et al., Automated in vivo quantification of emphysema. Radiology. Sep. 1993;188(3): 835-838. Retrieved from internet. Retrieved on Mar. 22, 2017.

(Continued)

*Primary Examiner* — Carl H Layno
*Assistant Examiner* — Michael J Lau
(74) *Attorney, Agent, or Firm* — Wilson Sonsini Goodrich & Rosati

(57) ABSTRACT

Devices, methods, and systems are provided for analyzing lung imaging data. A server computing device receives imaging data of a lung over a network from a client computing device and analyzes the imaging data to identify lung, airways, and blood vessels, segment the lung into lobes, subtract airways, calculate volumes, calculate emphysema scores, identify fissure locations, calculate fissure completeness scores. A reconstruction of the fissures indicating locations where the fissures are incomplete and a report comprising fissure scores, volumes, and emphysema scores are created.

27 Claims, 3 Drawing Sheets

(56) References Cited

U.S. PATENT DOCUMENTS

| | | | |
|---|---|---|---|
| 2004/0059263 A1* | 3/2004 | DeVore | A61B 5/1076 600/587 |
| 2005/0010445 A1* | 1/2005 | Krishnan | G06T 7/0012 705/2 |
| 2008/0009760 A1* | 1/2008 | Wibowo | A61B 5/02007 600/529 |
| 2009/0148008 A1* | 6/2009 | Wiemker | G06T 7/11 382/128 |
| 2010/0063410 A1* | 3/2010 | Avila | A61B 5/7275 600/532 |
| 2010/0070050 A1* | 3/2010 | Mathis | A61B 17/12131 623/23.65 |
| 2010/0310146 A1* | 12/2010 | Higgins | G06T 7/12 382/131 |
| 2012/0081362 A1* | 4/2012 | Kiraly | A61B 6/5241 345/419 |
| 2013/0004044 A1* | 1/2013 | Ross | G06T 7/136 382/131 |
| 2013/0208955 A1* | 8/2013 | Zhao | G06Q 50/22 382/128 |
| 2014/0105472 A1* | 4/2014 | Yin | A61B 5/08 382/128 |
| 2014/0161331 A1* | 6/2014 | Cohen | A61M 25/09 382/128 |
| 2014/0275952 A1* | 9/2014 | Monroe | G06T 19/00 600/407 |
| 2014/0307932 A1* | 10/2014 | Jacob | G06T 7/0012 382/131 |
| 2015/0089365 A1* | 3/2015 | Zhao | G06Q 10/1095 715/708 |
| 2015/0238270 A1* | 8/2015 | Raffy | A61B 5/7275 600/407 |
| 2015/0302602 A1* | 10/2015 | Wiemker | G06T 7/12 382/131 |
| 2015/0332454 A1* | 11/2015 | Yin | A61B 6/50 382/131 |
| 2015/0351714 A1* | 12/2015 | De Backer | A61N 5/10 600/427 |

OTHER PUBLICATIONS

International Search Report dated Apr. 12, 2017 for International Application No. PCT/US2017/016591.

Muller, NL et al., Density mask. An objective method to quantitate emphysema using computed tomography. chest. Oct. 1988; 94(4): 782-7.Retrieved from internet. Retrieved on Mar. 22, 2017.<http://journal.publications.chestnet.org/pdfaccess.ashr?url=/data/journals/chest/21584/>.

"IPRP for PCT/US2017/016591 dated Aug. 7, 2018".

M. Schuhmann Computed Tomography Predictors of Response to Endobronchial Valve Lung Reduction Treatment. Comparison with Chartis, vol. 191, No. 7, Apr. 1, 2015 pp. 767-774.

* cited by examiner

METHODS, SYSTEMS, AND DEVICES FOR ANALYZING LUNG IMAGING DATA

CROSS-REFERENCE TO RELATED APPLICATIONS

This application claims the benefit of U.S. Provisional No. 62/291,889, filed Feb. 5, 2016, the entire content of which is incorporated herein by reference.

FIELD OF THE INVENTION

The present disclosure relates generally to devices, methods, and systems for analyzing lung imaging data.

BACKGROUND

Pulmonary diseases, such as chronic obstructive pulmonary disease, (COPD), reduce the ability of one or both lungs to fully expel air during the exhalation phase of the breathing cycle. Such diseases are accompanied by chronic or recurrent obstruction to air flow within the lung. Because of the increase in environmental pollutants, cigarette smoking, and other noxious exposures, the incidence of COPD has increased dramatically in the last few decades and now ranks as a major cause of activity-restricting or bed-confining disability in the United States. COPD can include such disorders as chronic bronchitis, bronchiectasis, asthma, and emphysema.

It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the diseased (e.g., emphysematic) lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled, another factor that prevents full exhalation.

The problem is further compounded by the diseased, less elastic tissue that surrounds the very narrow airways that lead to the alveoli, which are the air sacs where oxygen-carbon dioxide exchange occurs. The diseased tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange.

In addition, hyper-expanded, diseased lung tissue occupies more of the pleural space than healthy lung tissue. In most cases, a portion of the lung is diseased while the remaining part is relatively healthy and, therefore, still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Some recent treatments include the use of devices that isolate a diseased region of the lung in order to reduce the volume of the diseased region, such as by collapsing the diseased lung region. According to such treatments, a delivery catheter is used to implant one or more implantable devices in airways feeding a diseased region of the lung to regulate fluid flow to the diseased lung region in order to fluidly isolate the region of the lung. These implantable devices can be, for example, one-way valves that allow flow in the exhalation direction only, occluders or plugs that prevent flow in either direction, or two-way valves that control flow in both directions.

In addition to the above, it is sometimes desirable to provide methods for sealing collateral flow channels between adjacent lung segments. Such sealing methods may be particularly useful for treating patients prior to endobronchial or other lung volume reduction procedures. Thus, methods and apparatus for sealing collateral flow channels should be compatible with known protocols for occluding diseased lung segments and regions for performing lung volume reduction, including the placement of plugs and occluding members within the airways leading to such diseased lung segments and regions. In other cases, sealing agents may be provided, though they are not equipped with the systems or methods for delivery for collateral channels.

Imaging techniques such as X-ray computed tomography (CT) may be used in assessment of disease and treatment planning. Disease and anatomical features of a lung may be difficult to determine through visual inspection of CT images. It is thus desirable to provide methods, systems, and devices for analyzing imaging data. At least some of these objectives will be met by the inventions described herein below.

SUMMARY OF THE INVENTION

The present disclosure relates to aspects of methods, devices, and systems for analyzing lung imaging data. In one aspect, a method for analyzing computerized tomography data of a lung is disclosed. Said method comprises receiving by a server computing device anonymized computerized tomography data of a lung over a network from a client computing device, analyzing the computerized tomography data, calculating a fissure completeness score for each fissure, creating a three-dimensional reconstruction of the fissures indicating locations where the fissures are incomplete, and creating a report comprising fissure scores, volumes, and emphysema scores. In an embodiment, the report may be delivered over the network to the client computing device. Analyzing the computerized tomography data may comprise identifying the lung, airways, and blood vessels, segmenting the lung into five separate lobes, subtracting airways until at least the third generation, calculating volumes of the lobes, calculating emphysema scores for the lobes based on density masks, and identifying fissure locations. The lung may be further segmented into separate lung segments or separate lung sub-segments. Volumes and emphysema scores may be calculated for lung segments or lung sub-segments. The fissure completeness score of the right upper lobe may be based on the completeness of the horizontal fissure and the portion of the right oblique fissure that separates the right upper lobe from the right lower lobe. The fissure completeness score of the right middle lobe may be based on the completeness of the horizontal fissure and the portion of the right oblique fissure that separates the right middle lobe from the right lower lobe.

The report may further comprise a two-dimensional graphical representation of the lung with the five lobes identified. The lobes may be shaded or colored in the two-dimensional graphical representation to indicate the emphysema score and the fissures may be identified in with lines that indicate completeness of the fissure.

The report may also comprise a three-dimensional graphical representation of the lung. Each lobe may be identified in the three-dimensional graphical representation with the lobes shaded or colored to indicate the emphysema score. In an embodiment, the report contains multiple two-dimensional graphical representations of cross sections of the lung. The three-dimensional graphical representation of the lung may be rotatable to view the lung from multiple viewing angles. The graphical representation may also identify lung segments and lung sub-segments.

Additionally, diameters for lobar bronchi, segmental bronchi, and sub-segmental bronchi may be determined. Distances from ostiums to a distal carinas may also be determined for the lobar bronchi, segmental bronchi, and sub-segmental bronchi. The report may contain the diameters and distances. The method may also include identifying which sub-segments are in contact with one of the locations where a fissure is incomplete. The report may indicate these identified sub-segments.

New anonymized computerized tomography data of the lung may be received by the server computing device over a network after treatment. Analysis of the new data and comparison of the lung after treatment to the lung before treatment may be done to determine treatment success. In an embodiment, patient selection, identification of regions of interest, or determination of treatment options may be improved through machine learning.

In another aspect, the report comprises patient selection information, personalized treatment planning information, identification of regions of interest, potential treatment site or suggested treatments. In an embodiment, the report comprises a potential treatment site and a suggested implantable device having a diameter and length matching the diameter and distance determined for the potential treatment site. In another embodiment, the report comprises a region of interest, a suggested therapeutic agent to be delivered, and a closest airway for treatment with the therapeutic agent. In one aspect, the report comprises airway navigation information for accessing the potential treatment sites. Navigation information may include a three-dimensional airway model and two-dimensional images of entrances to airways.

This and other aspects of the present disclosure are described herein.

BRIEF DESCRIPTION OF THE DRAWINGS

Present embodiments have other advantages and features which will be more readily apparent from the following detailed description and the appended claims, when taken in conjunction with the accompanying drawings, in which:

DETAILED DESCRIPTION OF THE INVENTION

Figure 1:
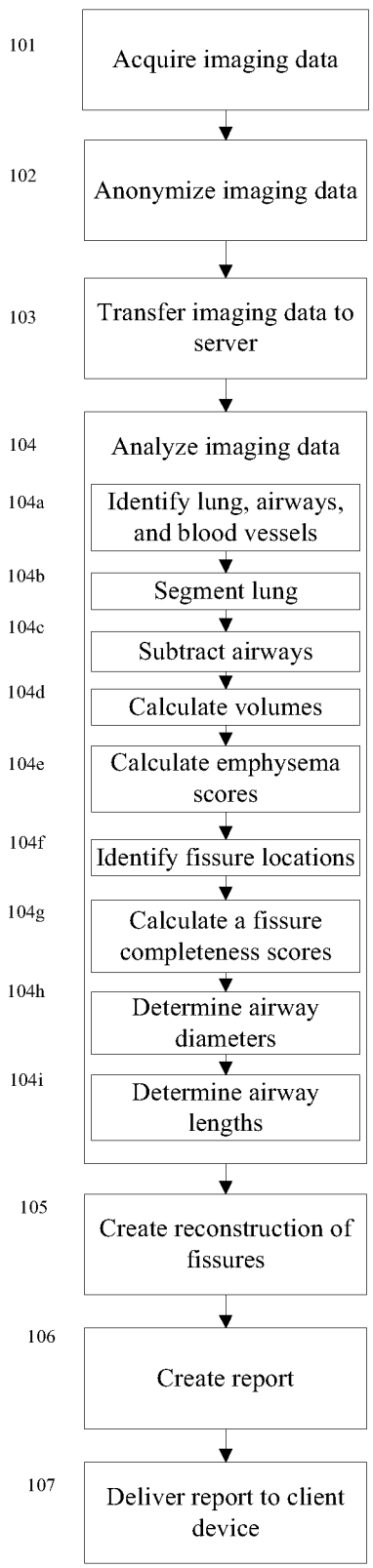
FIG. 1 shows a method for analyzing imaging data of a lung.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The word "exemplary" is used herein to mean "serving as an example, instance, or illustration." Any implementation described herein as "exemplary" is not necessarily to be construed as advantageous over other implementations.

The present disclosure describes methods, systems, and devices for analyzing CT data of a lung. While analysis of X-ray computed tomography (CT) data is described throughout, it is contemplated that other imaging data such as magnetic resonance imaging (MRI) data, 3D ultrasound data, positron emission tomography (PET) data, single-photon emission computed tomography (SPECT) data, etc. may be used additionally or alternatively.

Figure 2:
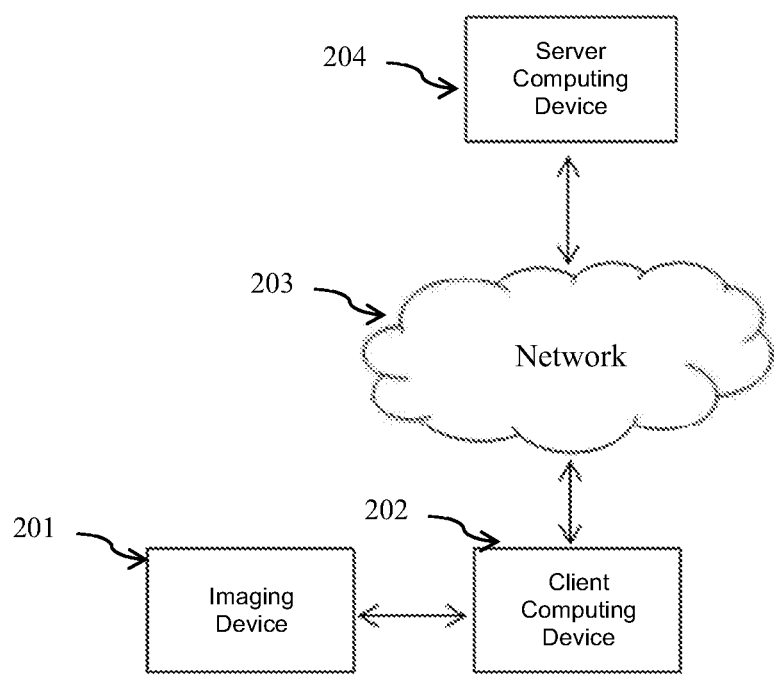
FIG. 2 shows an exemplary system architecture.

FIG. 1 shows a method for analyzing CT data of a lung. A corresponding exemplary system architecture is shown in FIG. 2. At step 101 a client device 202 acquires CT data of a lung from an imaging device 201. CT data may be of various formats such as Digital Imaging and Communications in Medicine (DICOM). At step 102 patient identifiable data is removed from the CT data on the client computing device 202 in order to anonymize the CT data. At step 103 anonymized CT data is transferred over network 203 to a server computing device 204.

At step 104 server computing device 204 analyzes the CT data. Methods for analyzing CT imaging data have been described in Kuhnigk, Jan-Martin, et al. "Informatics in radiology (infoRAD): new tools for computer assistance in thoracic CT. Part 1. Functional analysis of lungs, lung lobes, and bronchopulmonary segments." *Radiographics: a review publication of the Radiological Society of North America, Inc* 25.2 (2004): 525-536, Kuhnigk, Jan-Martin, et al. "Lung lobe segmentation by anatomy-guided 3D watershed transform." *Medical Imaging* 2003. International Society for Optics and Photonics, 2003, Zhang, Li, and Joseph M. Reinhardt. "Detection of lung lobar fissures using fuzzy logic." *Medical Imaging* '99. International Society for Optics and Photonics, 1999, Zhang, Li, and Joseph M. Reinhardt. "3D pulmonary CT image registration with a standard lung atlas." *Medical Imaging* 2000. International Society for Optics and Photonics, 2000, Qian, Jiang, Theophano Mitsa, and Eric A. Hoffman. "Elastic contour model-based analysis of structural deformations: toward time-sequenced regional lung parenchymal analysis." *Medical Imaging* 1996. International Society for Optics and Photonics, 1996, Reinhardt, Joseph M., et al. "Pulmonary imaging and analysis." *Handbook of medical imaging* 2 (2000): 1005-1060, Zhang, Li, Eric A. Hoffman, and Joseph M. Reinhardt. "Atlas-driven lung lobe segmentation in volumetric X-ray CT images." *Medical Imaging* 2003. International Society for Optics and Photonics, 2003, Zhang, Li, Eric A. Hoffman, and Joseph M. Reinhardt. "Lung lobe segmentation by graph search with 3D shape constraints." *Medical Imaging* 2001. International Society for Optics and Photonics, 2001, Marie-Pierre Revel, et al, Automated lobar quantification of emphysema in patients with severe COPD, European Radiology December 2008, Volume 18, Issue 12, pp 2723-2730, Wiemker, Rafael, Thomas Billow, and Thomas Blaffert. "Unsupervised extraction of the pulmonary interlobar fissures from high resolution thoracic CT data." International Congress Series. Vol. 1281. Elsevier, 2005, Xiao, C., et al. "Pulmonary Fissure Detection in CT Images Using a Derivative of Stick Filter." *IEEE transactions on medical imaging* (2016), Schmidt-Richberg, Alexander, et al. "Evaluation of Algorithms for Lung Fissure Segmentation in CT Images." Bildverarbeitung für die Medizin 2012. Springer Berlin Heidelberg, 2012. 201-206, Minder, Tobias, Hannes Wendland, and Rafael Wiemker. "Lobar fissure detection using line enhancing filters." SPIE Medical Imaging. International Society for Optics and Photonics, 2013, Lassen, Bianca, et al. "Lung and lung lobe segmentation methods at Fraunhofer MEVIS." *4th Int. MIC-CAI Workshop Pulmonary Image Anal., Toronto, Canada*, 2011, Lassen, Bianca, et al. "Automatic segmentation of lung lobes in CT images based on fissures, vessels, and bronchi." *Biomedical Imaging: From Nano to Macro*, 2010 IEEE International Symposium on. IEEE, 2010, Lassen, Bianca, et al. "Interactive lung lobe segmentation and correction in tomographic images." *SPIE Medical Imaging*, International Society for Optics and Photonics, 2011, Revel, Marie-Pierre, et al. "Automated lobar quantification of emphysema in patients with severe COPD." *European radiology* 18.12 (2008): 2723-2730, Sluimer, Ingrid, Mathias Prokop, and Bram Van Ginneken. "Toward automated segmentation of the pathological lung in CT." *Medical Imaging, IEEE Transactions on* 24.8 (2005): 1025-1038.c, the full disclosures of which are hereby incorporated by reference.

Optionally, quality control checks may be performed to ensure scans are of adequate quality for processing. Analysis of the CT data may comprise some or all of steps 104a-104i. Some or all of steps 104a-104i may be performed sequentially in various orders. Additionally or alternatively, some or all of steps 104a-104i may be performed in parallel. At step 104a server computing device 204 identifies the lung, airways, and blood vessels using the CT data.

At step 104b server computing device 204 segments the lung. In an embodiment the lung is segmented into five separate lobes, the right upper lobe, the right middle lobe, the right lower lobe, the left upper lobe, and the left upper lobe. Each lobe may be further segmented into separate lung segments. Lung segments may also be further segmented into separate lung sub-segments.

At step 104c server computing device 204 subtracts the airways. In an embodiment, airways are subtracted until the third generation. In other embodiments, more or less generations of airways may be subtracted.

At step 104d server computing device 204 calculates volumes of the lobes. In an embodiment, volumes of separate lung segments may be calculated. Server computing device 204 may also calculate volumes of separate lung sub-segments.

At step 104e server computing device 204 calculates emphysema scores for the lobes. Emphysema scores may be calculated using density masks at various user defined thresholds, for example, −910 Hounsfield or −950 Hounsfield units. In an embodiment, emphysema scores for separate lung segments may be calculated. Server computing device 204 may also calculate emphysema scores for separate lung sub-segments.

At step 104f server computing device 204 identifies fissure locations. At step 104h server computing device 204 identifies fissure completeness for each fissure or portions of each fissure. Fissure completeness scores are calculated for each lobe. Fissure completeness scores may represent the percentage complete of the portions of the fissures touching each lobe. For example, the fissure completeness score of the right upper lobe may be based on the completeness of the horizontal fissure and the completeness of the portion of the right oblique fissure that separates the right upper lobe from the right lower lobe. Similarly, the fissure completeness score of the right middle lobe may be based on the completeness of the horizontal fissure and the completeness of the portion of the right oblique fissure that separates the right middle lobe from the right lower lobe.

At step 104h server computing device 204 may determine airway diameters. In an embodiment, diameters for lobar bronchi, segmental bronchi, and sub-segmental bronchi are determined for each lobe. At step 104i server computing device 204 may determine airway lengths. In an embodiment distances from an ostium to a distal carina may be determined for lobar bronchi, segmental bronchi, and sub-segmental bronchi.

At step 105 server computing device 204 creates a three-dimensional reconstruction of the fissures indicating locations where the fissures are incomplete. In an embodiment, the reconstruction of the fissures may be color coded or comprise a heat map to indicate completeness. At step 106 server computing device 204 creates a report comprising fissure scores, volumes, and emphysema scores for each lobe. The report may be exportable in various electronically viewable or printable formats such as Portable Document Format (PDF), word processing documents, images such as JPEG, videos, etc. In an embodiment, the report comprises fissure scores, volumes, and emphysema scores for separate lung segments. The report may also comprise fissure scores, volumes, and emphysema scores for separate lung sub-segments. The report may also comprise the three-dimensional reconstruction of the fissures.

Figure 3:
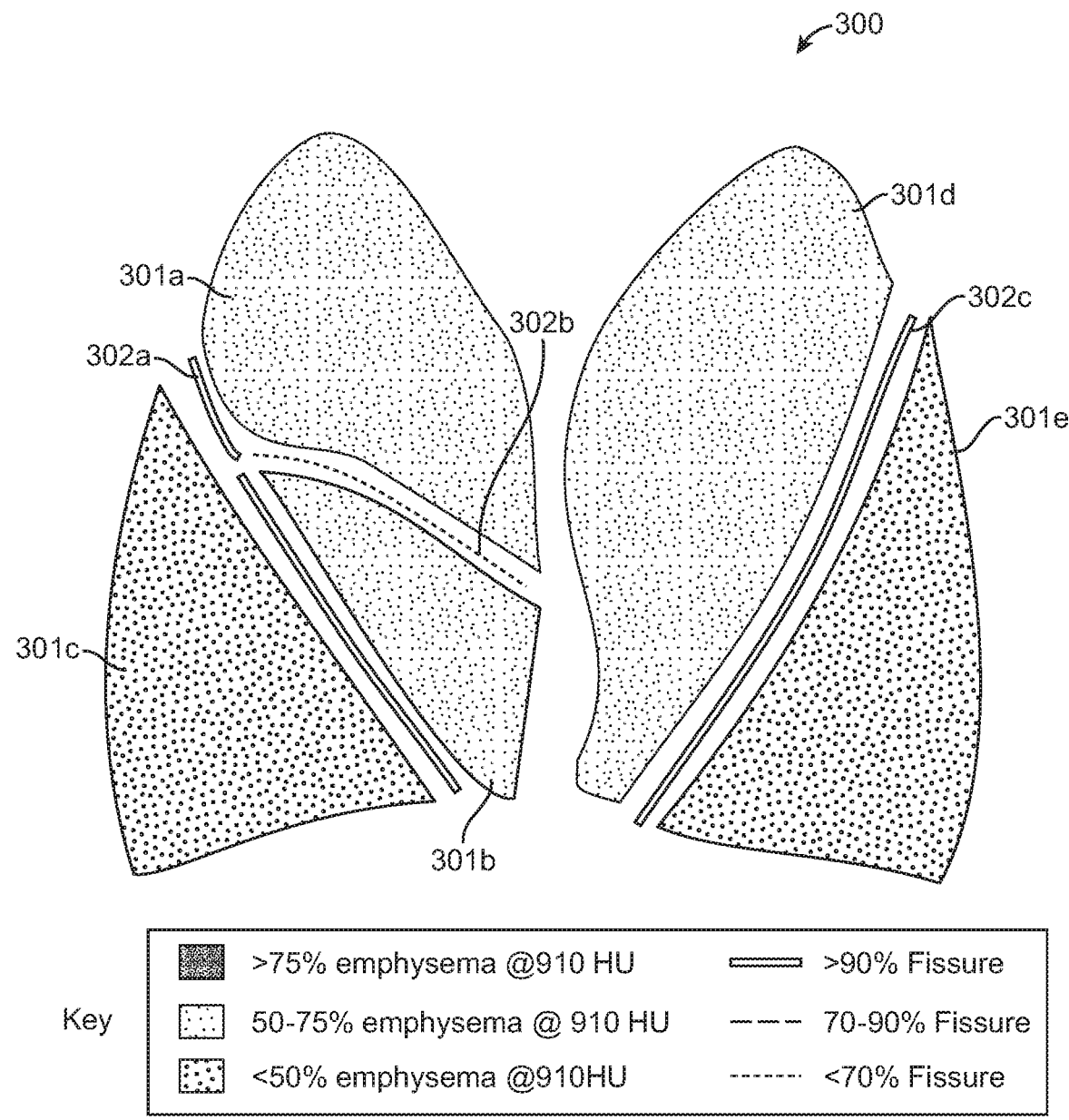
FIG. 3 shows an exemplary graphical representation of a lung indicating emphysema score and fissure completeness.

FIG. 3 shows an exemplary graphical representation of a lung included in the report. The report may comprise a two-dimensional graphical representation of the lung 300 with the five lobes 301a-301e identified. The lobes 301a-301e are shaded or colored in the two-dimensional graphical representation to indicate the emphysema score. Fissures 302a-302c may be identified in the two-dimensional graphical representation with lines that indicate completeness of the fissure 302a-302c. Fissure lines may have varying shading, color coding, thickness, or solid versus dashed lines to indicate completeness of the fissure 302a-302c. Fissures 302a-302c may be classified into different categories with different line types based on the completeness of the fissure 302a-302c for that location. In an embodiment, fissures 302a-302c receive a first type of line if they have high completeness with a fissure score greater than a specified fissure percent complete (e.g., >95%), a second type of line if they have low completeness with a fissure score less than specified fissure percent complete (e.g., <80%), or a third type of line if they have intermediate completeness with a fissure score specified percent complete defined as between high and low completeness scores (e.g., between 80% to 95%).

The report may further comprise a three-dimensional graphical representation of the lung with each lobe identified. Lobes may be shaded or colored in the three-dimensional graphical representation to indicate the emphysema score. In an embodiment, the three-dimensional graphical representation of the lung may identify each lung segment and/or each lung sub-segment. Lung segments and/or lung sub-segments may be shaded or colored in the three-dimensional graphical representation to indicate the emphysema score. Fissures may be identified in the three-dimensional graphical representation with lines that indicate completeness of the fissure. In an embodiment, the report contains multiple two-dimensional graphical representations of cross sections of the lung. The three-dimensional model may be provided as a video or interactive model wherein the lung is rotatable to view lung model from multiple viewing angles.

The report may be annotated and customized for the specific lung. Annotation and customization may include patient selection information, personalized treatment planning information, identification of regions of interest, potential treatment sites, and/or suggested treatments.

The report may comprise treatment suggestions for using implantable devices such as endobronchial valves, clips, or plugs. In an embodiment, the implantable device is a one-way flow control valve configured to allow air to flow out of the target lung compartment and prevent air flow into the target lung compartment, thus causing volume reduction or collapse of the target lung region. Examples of such implants and methods are described, for example, in U.S. Pat. Nos. 8,136,526 and 7,798,147, the full disclosures of which are hereby incorporated by reference. In an embodiment, the report contains the airway diameters and distances determined in steps 104h and 104i. Server computing device 204 may be configured to compare the determined diameters and distances to known diameters and lengths of implantable devices and create a treatment plan with potential treatment sites based on an ideal combination of devices to be placed. The report may include potential treatment sites and suggested implantable devices having diameters and lengths matching the diameters and distances determined for the potential treatment sites.

Additionally or alternatively, the report may comprise treatment suggestions for using therapeutic agents such as sealants. Examples of such therapeutic agents and methods are described, for example, in U.S. Pat. Nos. 8,137,302, 7,819,908 and 8,445,589, the full disclosures of which are hereby incorporated by reference. Server computing device 204 may be configured to identifying which lung segments or lung sub-segments are in contact with one of the locations where a fissure is incomplete. The report may indicate the identified lung segments or lung sub-segments in contact with a location where a fissure is incomplete. The report may also include suggested therapeutic agents to be delivered at identified lung segments or lung sub-segments in contact with a location where a fissure is incomplete. In an embodiment, user-selectable regions of interest are provided with identified closest airways for treatment with the therapeutic agent.

With any of the suggested treatment options, the report may comprise navigation information for accessing potential treatment sites. In an embodiment, the report comprises a three-dimensional airway model. Additionally or alternatively, the report may comprise a two-dimensional image of an entrance to each airway. The report may also provide a video fly-through and/or two dimensional turn-by-turn steps for accessing the region of interest from the trachea.

At step 107 server computing device 204 delivers the report to client device 202 or other computing device over the network. Optionally, user identifiable information removed at step 102 may be added to the report on the client device 202.

Optionally steps 101 through 107 may be repeated after treatment. Results may be used to compare the lung before and after treatment in order to determine treatment success. In an embodiment, the determined treatment success may be used as feedback to improve future patient selection, identification of regions of interest, and/or determination of treatment options through machine learning.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus or system for performing the operations herein. This apparatus or system may be specially constructed for the required purposes, and/or it may comprise a general-purpose computing device selectively activated or reconfigured by a computer program stored in a computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Imaging device 201, client computing device 202, and server computing device 204 shown in FIG. 2 may comprise various components including but not limited to one or more processing units, memory units, video or display interfaces, network interfaces, input/output interfaces and buses that connect the various units and interfaces. The network interfaces enable the imaging device 201, client computing device 202, and/or server computing device 204 to connect to the network 203. The memory units may comprise random access memory (RAM), read only memory (ROM), electronic erasable programmable read-only memory (EEPROM), and basic input/output system (BIOS). The memory unit may further comprise other storage units such as non-volatile storage including magnetic disk drives, optical drives, flash memory and the like.

While FIG. 2 depicts one imaging device 201, one client computing device 202, one network 203, and one server computing device 204, this is meant as merely exemplary. Alternatively, any number of imaging devices 201, client computing devices 202, networks 203, or server computing devices 204 may be present. Some or all of the components of imaging device 201, client computing device 202, and/or server computing device 204 may be combined into a single device. Likewise, some or all of the components of imaging device 201, client computing device 202, and/or server computing device 204 may be separated into distinct devices connected through the network 203 or other connection methods.

The various devices depicted in FIG. 2 may comprise computing devices or reside on computing devices such as servers, desktop computers, laptop computers, tablet computers, personal digital assistants (PDA), smartphones, mobile phones, smart devices, appliances, sensors, or the like. Computing devices may comprise processors, memories, network interfaces, peripheral interfaces, and the like.

The various devices in FIG. 2 may be configured to communicate directly or indirectly with a wireless network such as through a base station, a router, switch, or other computing devices. In an embodiment, the components may be configured to utilize various communication protocols such as Global System for Mobile Communications (GSM), General Packet Radio Services (GPRS), Enhanced Data GSM Environment (EDGE), Code Division Multiple Access (CDMA), Wideband Code Division Multiple Access (WCDMA), Bluetooth, High Speed Packet Access (HSPA), Long Term Evolution (LTE), and Worldwide Interoperability for Microwave Access (WiMAX).

The devices may be further configured to utilize user datagram protocol (UDP), transport control protocol (TCP), Wi-Fi, satellite links and various other communication protocols, technologies, or methods. Additionally, the devices may be configured to connect to an electronic network without communicating through a wireless network. The devices may be configured to utilize analog telephone lines (dial-up connection), digital lines (T1, T2, T3, T4, or the like), Digital Subscriber lines (DSL), Ethernet, or the like. It is further contemplated that the devices may be connected directly to a computing device through a USB port, Bluetooth, infrared (IR), Firewire port, thunderbolt port, ad-hoc wireless connection, or the like. Devices may be configured to send, receive, and/or manage messages such as email, SMS, IM, MMS, or the like.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for analyzing computerized tomography data of a lung, the method comprising:
   receiving by a server computing device anonymized computerized tomography data of a lung over a network from a client computing device at a different location;
   analyzing the computerized tomography data, wherein analyzing the computerized tomography data comprises
   identifying the lung, airways, and blood vessels;
   segmenting the lung into five separate lobes;
   subtracting airways until at least the third generation;
   calculating volumes of the lobes;
   calculating emphysema scores for the lobes based on density masks; identifying fissure locations;
   calculating a fissure completeness score for each fissure, wherein the fissure completeness score of the right upper lobe is based on the completeness of the horizontal fissure and the portion of the right oblique fissure that separates the right upper lobe from the right lower lobe, and wherein the fissure completeness score of the right middle lobe is based on the completeness of the horizontal fissure and the portion of the right oblique fissure that separates the right middle lobe from the right lower lobe;
   creating a three-dimensional reconstruction of the fissures indicating locations where the fissures are incomplete; and
   creating a report comprising fissure completeness scores, volumes, and emphysema scores for each lobe.

2. The method of claim 1, further comprising delivering the report over the network to the client computing device.

3. The method of claim 1, wherein the report comprises patient selection information.

4. The method of claim 1, wherein the report comprises personalized treatment planning information.

5. The method of claim 4, wherein personalized treatment planning information comprises identification of regions of interest.

6. The method of claim 4, wherein personalized treatment planning information comprises potential treatment sites and suggested treatments for the potential treatment sites.

7. The method of claim 1, further comprising receiving new anonymized computerized tomography data of the lung by the server computing device over a network after treatment;
   analyzing the new anonymized computerized tomography data; and
   comparing the lung after treatment to the lung before treatment to determine treatment success.

8. The method of claim 7, further comprising improving patient selection, identification of regions of interest, or determination of treatment options through machine learning.

9. The method of claim 1, further comprising determining airway diameters for lobar bronchi, segmental bronchi, and sub-segmental bronchi for each lobe; and
   determining a distance from an ostium to a distal carina for the lobar bronchi, segmental bronchi, and sub-segmental bronchi;
   wherein the report contains the determined airway diameters and distances.

10. The method of claim 9, wherein the report comprises a three-dimensional airway model.

11. The method of claim 9, wherein the report comprises a two-dimensional image of an entrance to an airway.

12. The method of claim 9, wherein the report comprises a potential treatment site and a suggested implantable endobronchial valve having a diameter and length matching the diameter and distance determined for the potential treatment site.

13. The method of claim 12 wherein the report comprises airway navigation information for accessing the potential treatment site, wherein the navigation information comprises turn-by-turn steps for accessing the potential treatment site.

14. The method of claim 1, wherein the report further comprises a two-dimensional graphical representation of the lung with the five lobes identified;
   wherein the lobes are shaded or colored in the two-dimensional graphical representation to indicate the emphysema score; and
   wherein the fissures are identified in the two-dimensional graphical representation with lines that indicate the fissure completeness scores.

15. The method of claim 14, wherein the lines that indicate fissure completeness scores are classified into different fissure completeness score categories with different line types based on the fissure completeness score; wherein the fissure completeness categories comprise a high completeness category corresponding to a fissure completeness score greater than a first predetermined value, a low completeness category corresponding to a fissure completeness score less than a second predetermined value, and an intermediate completeness category corresponding fissure completeness score between the first and second predetermined values.

16. The method of claim 14, wherein the fissure line have shading, color, thickness, or solid versus dashed line to indicate the fissure completeness scores.

17. The method of claim 14, wherein the report further comprises a three-dimensional graphical representation of the lung;
   wherein each lobe is identified in the three-dimensional graphical representation;
   wherein the lobes are shaded or colored in the three-dimensional graphical representation to indicate the emphysema score; and wherein the report contains multiple two-dimensional graphical representations of cross sections of the lung.

18. The method of claim 17, wherein the three-dimensional graphical representation of the lung is rotatable to view the lung from multiple viewing angles.

19. The method of claim 17, wherein the fissures are identified in the three-dimensional graphical representation with lines that indicate the fissure completeness scores.

20. The method of claim 17, wherein the fissures are identified in the two-dimensional graphical representations of cross sections of the lung with lines that indicate the fissure completeness scores.

21. The method of claim 1, wherein analyzing the computerized tomography data further comprises segmenting the each lobe into separate lung segments;
    calculating volumes of the lung segments; and
    calculating emphysema scores for the segments based on density masks; and
    wherein the report comprises volumes and emphysema scores for each lung segment.

22. The method of claim 21, wherein analyzing the computerized tomography data further comprises segmenting each lung segment into separate lung sub-segments;
    calculating volumes of the lung sub-segments; and
    calculating emphysema scores for the sub-segments based on density masks;
    wherein the report comprises volumes and emphysema scores for each lung sub-segment.

23. The method of claim 22, wherein the report further comprises a three-dimensional graphical representation of the lung;
    wherein each lung segment and lung sub-segment is identified in the three-dimensional graphical representation;
    wherein the lung segments and lung sub-segments are shaded or colored in the three-dimensional graphical representation to indicate the emphysema score; and
    wherein the report contains multiple two-dimensional graphical representations of cross sections of the lung.

24. The method of claim 22, wherein the report comprises a region of interest in contact with a location where a fissure is incomplete, a suggested therapeutic agent to be delivered at the region of interest, and a closest airway for treatment of the region of interest with the therapeutic agent, wherein the therapeutic agent is a sealant.

25. The method of claim 24, wherein the report comprises airway navigation information for accessing the region of interest, wherein the navigation information comprises turn-by-turn steps for accessing the region of interest.

26. The method of claim 22, further comprising identifying which sub-segments are in contact with one of the locations where a fissure is incomplete;
    wherein the report indicates the identified sub-segments in contact with a location where a fissure is incomplete.

27. The method of claim 26, wherein the report comprises airway navigation information for accessing the location where the fissure is incomplete.

* * * * *